United States Patent
Kim et al.

(10) Patent No.: US 9,532,866 B2
(45) Date of Patent: Jan. 3, 2017

(54) ACELLULAR DERMAL GRAFT

(71) Applicants: L&C BIO CO., LTD., Seongnam-si Gyeonggi-do (KR); Joon Yong Kim, Boondang-gu Seongnam-si Gyeonggi-do (KR); Byung Moo Kim, Boondang-gu Seongnam-si Gyeonggi-do (KR)

(72) Inventors: Joon Yong Kim, Seongnam-si (KR); Byung Moo Kim, Seongnam-si (KR); Yong Sup Hwang, Seoul (KR); Whan Chul Lee, Yongin-si (KR); Soo Jeong Seo, Seongnam-si (KR); Ju Hee Lee, Newton, MA (US); Hyung Gu Kim, Seoul (KR)

(73) Assignee: L&C BIO CO., LTD., Seongnam-si, Gyeonggi-Do (KR)

( * ) Notice: Subject to any disclaimer, the term of this patent is extended or adjusted under 35 U.S.C. 154(b) by 36 days.

(21) Appl. No.: 14/484,031

(22) Filed: Sep. 11, 2014

(65) Prior Publication Data
US 2015/0057751 A1     Feb. 26, 2015

Related U.S. Application Data

(63) Continuation of application No. PCT/KR2013/002063, filed on Mar. 14, 2013.

(30) Foreign Application Priority Data

Mar. 15, 2012  (KR) .................. 10-2012-0026616
Mar. 15, 2012  (KR) .................. 10-2012-0026617
(Continued)

(51) Int. Cl.
A61F 2/10     (2006.01)

(52) U.S. Cl.
CPC .................... A61F 2/105 (2013.01)

(58) Field of Classification Search
CPC .................... A61L 27/60; A61L 2/105
(Continued)

(56) References Cited

U.S. PATENT DOCUMENTS 5,489,304 A * 2/1996 Orgill ............. A61L 27/60
                                               128/898
5,618,528 A * 4/1997 Cooper ........ A61K 47/48215
                                               424/78.3
(Continued)

FOREIGN PATENT DOCUMENTS

| EP | 1020198 B1 | 7/2006 |
|---|---|---|
| JP | 3658385 B2 | 6/2005 |
| KR | 10-2001-00092985 A | 10/2001 |

*Primary Examiner* — Suzette J Gherbi
(74) *Attorney, Agent, or Firm* — Elie Gendloff; TechLaw LLP

(57) ABSTRACT

An acellular dermal graft is provided. The acellular dermal graft may be useful in minimizing side effects caused after transplantation since an environment favorable for formation of new blood vessels and proliferation of autologous tissues is provided by forming a multi-penetration structure in an acellular dermal tissue, removing a basement membrane layer and/or subjecting corners to slope cutting, and transplantation is stably performed within a short transplantation time due to improved extensibility and flexibility of tissues. The acellular dermal graft may be useful in reducing a time required to recover tissues after transplantation since the transplantation is stably performed due to improved grafting reaction with a host tissue by enhancing uptake of fibroblasts and promoting angiogenic activities. Also, the acellular dermal graft may be useful in maintaining smooth external appearance since hypodermic implantation is easily performed upon transplantation, and the skin at a graft site does not protrude after transplantation.

10 Claims, 12 Drawing Sheets

(30) Foreign Application Priority Data

| | | |
|---|---|---|
| Mar. 15, 2012 | (KR) | 10-2012-0026618 |
| Jun. 15, 2012 | (KR) | 10-2012-0064022 |
| Jun. 15, 2012 | (KR) | 10-2012-0064024 |
| Jun. 15, 2012 | (KR) | 10-2012-0064026 |
| Mar. 14, 2013 | (WO) | PCT/KR2013/002063 |

(58) Field of Classification Search
USPC .......................................... 623/15.12, 23.72
See application file for complete search history.

(56) References Cited

U.S. PATENT DOCUMENTS

| | | | | |
|---|---|---|---|---|
| 6,022,862 | A * | 2/2000 | Haimes | A61K 31/704 514/33 |
| 7,795,027 | B2 * | 9/2010 | Hiles | A61K 35/37 435/395 |
| 2005/0021141 | A1 | 1/2005 | Bleyer et al. | |
| 2010/0137902 | A1 * | 6/2010 | Lee | A61L 24/001 606/213 |
| 2010/0137903 | A1 * | 6/2010 | Lee | A61K 31/765 606/213 |
| 2012/0310335 | A1 * | 12/2012 | Matheny | A61F 2/2412 623/2.15 |
| 2012/0310367 | A1 * | 12/2012 | Connor | A61K 35/35 623/23.72 |
| 2012/0329034 | A1 * | 12/2012 | Chun | A61L 27/362 435/1.3 |
| 2013/0005699 | A1 * | 1/2013 | Bar-Or | A61K 31/00 514/176 |
| 2013/0116799 | A1 * | 5/2013 | Derwin | A61F 2/02 623/23.72 |
| 2013/0123938 | A1 * | 5/2013 | Ram-Liebig | A61L 27/24 623/23.72 |
| 2013/0247517 | A1 * | 9/2013 | Samaniego | A61L 27/3604 53/431 |
| 2013/0248386 | A1 * | 9/2013 | Benoit | A61F 2/0063 206/205 |
| 2013/0302436 | A1 * | 11/2013 | Wilhelmi | A61L 27/362 424/574 |
| 2013/0304098 | A1 * | 11/2013 | Mortarino | A61F 2/12 606/151 |
| 2013/0323201 | A1 * | 12/2013 | Wise | A61K 38/2066 424/85.2 |
| 2013/0337038 | A1 * | 12/2013 | Hocking | A61K 38/39 424/446 |
| 2014/0227347 | A1 * | 8/2014 | Bar-Or | A61K 31/58 424/450 |
| 2014/0300862 | A1 * | 10/2014 | Perez | A61B 3/102 351/206 |
| 2014/0343688 | A1 * | 11/2014 | Morse | A61L 27/3604 623/23.72 |
| 2015/0230913 | A1 * | 8/2015 | Derwin | A61F 2/02 623/23.72 |
| 2015/0352254 | A1 * | 12/2015 | Matheny | A61L 27/58 424/426 |

* cited by examiner (a)  (b)  (c)

ACELLULAR DERMAL GRAFT

CROSS-REFERENCE TO RELATED APPLICATION

This application is a continuation of International Application No. PCT/KR2013/002063, filed Mar. 14, 2013, which claims priority to Korean Patent Application No. 2012-0026616, filed Mar. 15, 2012, and to Korean Patent Application No. 2012-0026617, filed Mar. 15, 2012, and to Korean Patent Application No. 2012-0026618, filed Mar. 15, 2012, and to Korean Patent Application No. 2012-0064022, filed Jun. 15, 2012, and to Korean Patent Application No. 2012-0064024, filed Jun. 15, 2012, and to Korean Patent Application No. 2012-0064026, filed Jun. 15, 2012, the disclosures of which are incorporated herein by reference in their entirety.

BACKGROUND

Field of the Invention

The present invention relates to an acellular dermal graft, and a method of preparing the same.

Discussion of Related Art

Skin tissues of a human body are mainly divided into three parts: epidermis composed of the outermost layers of cells in the skin; dermis lined under the epidermis; and subcutaneous tissue. Among these, the epidermis is composed of epithelial cells in which a basement membrane capable of strongly binding the dermis to the epidermis is differentiated into various layers, and the other components such as melanocytes, and immune cells, and the dermis lined under the epidermis is composed mainly of fibroblasts and various extracellular matrixes secreted from the fibroblasts.

Some skin tissues or internal organ tissues may be injured by burns, external wounds, sores, etc. Here, a method of transplanting the patient's own skin tissue or internal organ tissue is used to heal the injured tissue or to carry out reconstructive plastic surgery. In this case, since skin tissue or organ tissue should be extracted from the patient who is to receive the transplant, the patient must undergo a substantial amount of surgery. It may be dangerous to carry out transplantation when the patient is not healthy. In addition, there is a method of performing transplantation using a xenograft or synthetic biomaterial. In this case, the patient may receive additional surgery due to an inflammatory response caused by an immune rejection response when the patient carries the transplant for a long period of time. To solve the problem, a method of preparing an acellular dermis for transplantation from a skin tissue extracted from a donor (Korean Patent Publication No. 2001-0092985, and Korean Patent No. 791502) and performing an operation is used as a method used to solve the difficulties.

Basically, when a graft is inserted in a host tissue of a human body, the graft causes various problems such as blockage of blood flow and bodily fluid circulation between the host tissue and the graft, blockage of blood circulation around the graft due to a compact structure of an extracellular matrix in the graft, the presence of a basement membrane layer, and a relatively higher thickness of the graft, blockage of bodily fluid circulation, a decrease in generation and migration of new blood vessels, restriction of proliferation of fibroblasts and endogenous collagen tissues, a foreign body sensation caused by an insufficient graft response, increased tendency for inflammation and infection, formation of a capsule of scar tissue around the graft, retention of bodily fluids, etc.

In the case of the acellular dermal tissue, the basement membrane layer is lined on an upper portion of the dermis, serves to strongly bind the dermis to the epidermis, and is attached to the dermis after removal of the epidermis. The basement membrane layer has a problem in that it may be slowly engrafted since its compact tissue significantly reduce an uptake rate of fibroblasts in the established graft site after transplantation, compared with other sites where no grafting is done.

In particular, most currently commercially available acellular dermal grafts have a problem in that they are transplanted in a quadrilateral shape, and thus the skin protrudes at the corners of the quadrilateral graft lined toward the surface of the skin, which leads to an unnatural external appearance. Also, since the front and rear surfaces of graft are not easily discriminated between with the unaided eye (for example, the basement membrane layer has a smooth surface, and a lower surface of the derma has a finely coarse surface), it is very difficult to find a way to discriminate between the front and rear surfaces of graft as required for transplantation. For rapid recovery of a patient after transplantation, it is also necessary to minimize skin incision at a graft site. In this case, a quadrilateral graft may not be easily grafted onto the graft site.

SUMMARY OF THE INVENTION

Accordingly, the present inventors have found that transplantation is stably performed by forming multiple penetrations in a preexisting acellular dermal tissue for transplantation, thereby enhancing extensibility and flexibility of tissues.

The present inventors have also found that, since an uptake rate of fibroblasts in an established graft site is significantly reduced after transplantation compared with other sites where no grafting is done, the fibroblast uptake rate may be maintained the same as for fibroblasts in sites having no basement membrane layer formed in a lower end and lateral portion thereof by removing a basement membrane layer reducing a grafting rate. In case of an acellular dermal tissue graft used so far, the basement membrane layer mostly appears at one side of the graft, and thus provides an unfavorable environment for fibroblasts to penetrate into and grow in the graft upon transplantation of the graft into a human body, thereby providing an unfavorable environment for the transplantation. Therefore, the present inventor can design an acellular dermal tissue graft from which such a basement membrane layer is removed to induce rapid infiltration and growth of the fibroblasts in a transplantation procedure after insertion of the graft.

Therefore, the present invention is directed to providing an acellular dermal graft capable of preventing formation of a dead space by forming multiple penetrations in an acellular dermal tissue to provide an environment favorable for the formation of new blood vessels and proliferation of autologous tissues, and minimizing side effects caused after transplantation since extensibility and flexibility of tissues is enhanced to stably and swiftly perform the transplantation.

Also, the present invention is directed to providing an acellular dermal graft capable of enhancing uptake of fibroblasts after transplantation by removing a basement membrane layer therefrom, and promoting angiogenic activities to increase a grafting rate onto the skin, thereby stably performing transplantation and shortening a time required for recovery after the transplantation.

In addition, the present invention is directed to providing a novel acellular dermal graft capable of maintaining a smooth external appearance without protrusion of the skin at the graft site after transplantation, as well as improving convenience of hypodermic implantation upon transplantation by slope-cutting corner portions of the acellular dermal tissue.

To solve the problems, one aspect of the present invention provides an acellular dermal graft having multiple penetrations formed therein, and a method of preparing the same.

To solve the problems, another aspect of the present invention provides an acellular dermal graft having corner portions slope-cut therein, and a method of preparing the same.

To solve the problems, still another aspect of the present invention provides an acellular dermal graft having a basement membrane layer removed therefrom, and a method of preparing the same.

BRIEF DESCRIPTION OF THE DRAWINGS

The above and other objects, features and advantages of the present invention will become more apparent to those of ordinary skill in the art by describing in detail exemplary embodiments thereof with reference to the adhered drawings, in which.

DETAILED DESCRIPTION OF EXEMPLARY EMBODIMENTS

Hereinafter, exemplary embodiments of the present invention will be described in detail. However, the present invention is not limited to the embodiments disclosed below, but can be implemented in various forms. The following embodiments are described in order to enable those of ordinary skill in the related art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

The present invention is directed to providing an acellular dermal graft having the following (1), (2) and/or (3) characteristics:

1) Forming multiple penetrations
2) Slope-cutting corner portions
3) Removing a basement membrane layer The acellular dermal graft may be skin, ligament, or cartilage, but the present invention is not limited thereto.

First, the acellular dermal graft according to the present invention may have a multi-penetration structure.

The multi-penetration structure refers to a vertical-axis multi-penetration structure and/or an alternately stacked, horizontal-axis multi-penetration structure.

The multi directional multi-penetration structure refers to containing a vertical-axis multi-penetration structure and an alternately stacked, horizontal-axis multi-penetration structure.

The vertical-axis penetration structure includes a multi-slit pattern and/or a multi-puncture pattern formed in the acellular dermal graft.

Figure 1:
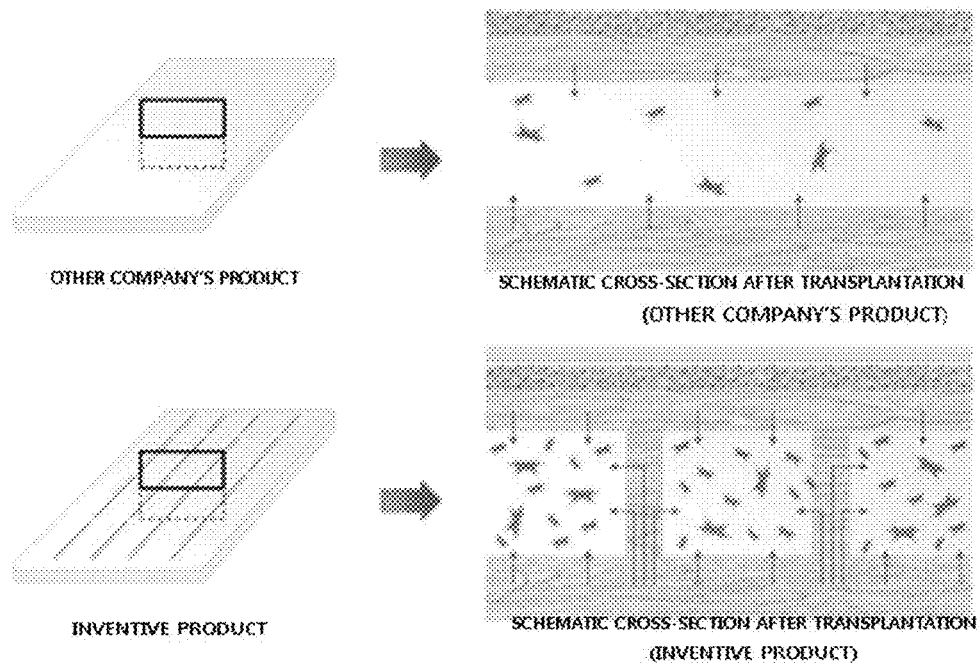
FIG. 1 is a diagram showing results obtained by comparing an acellular dermal graft (with multiple slits) according to one exemplary embodiment of the present invention with a conventional acellular dermal graft (Alloderm®, LifeCell Corporation, Branchburg, N.J.).
Figure 4:
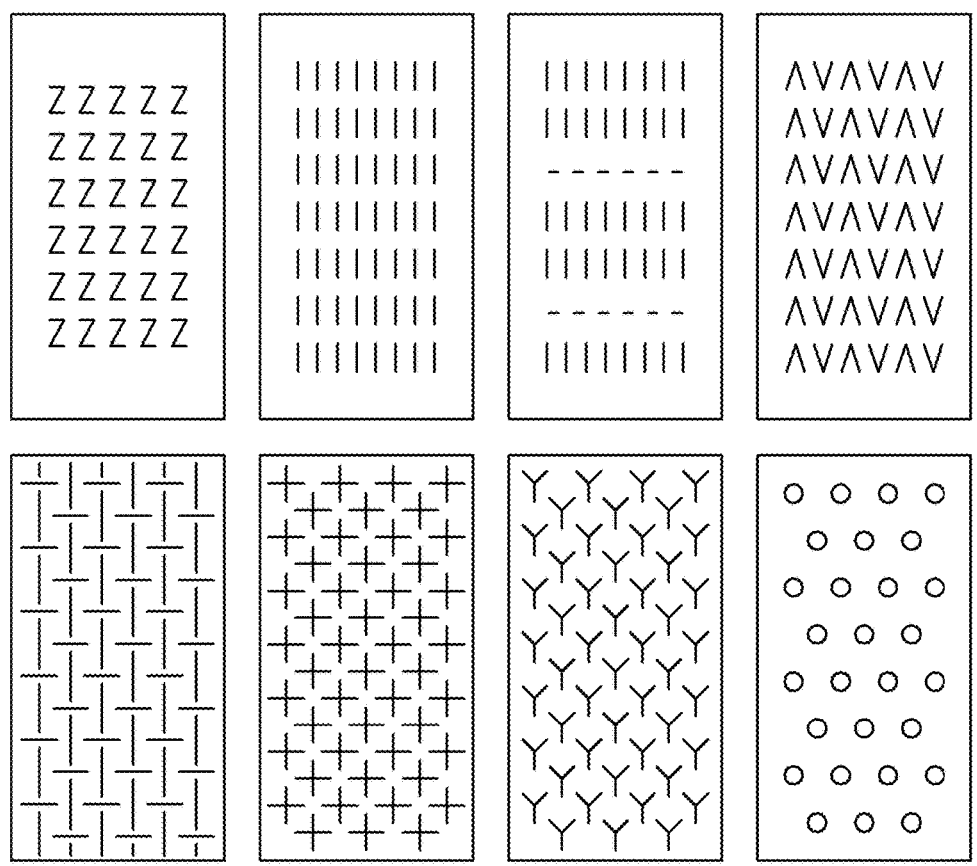
FIG. 4 is a plan view showing a graft having various kinds of multi-slit patterns and multiple punctures formed therein.
Figure 5:
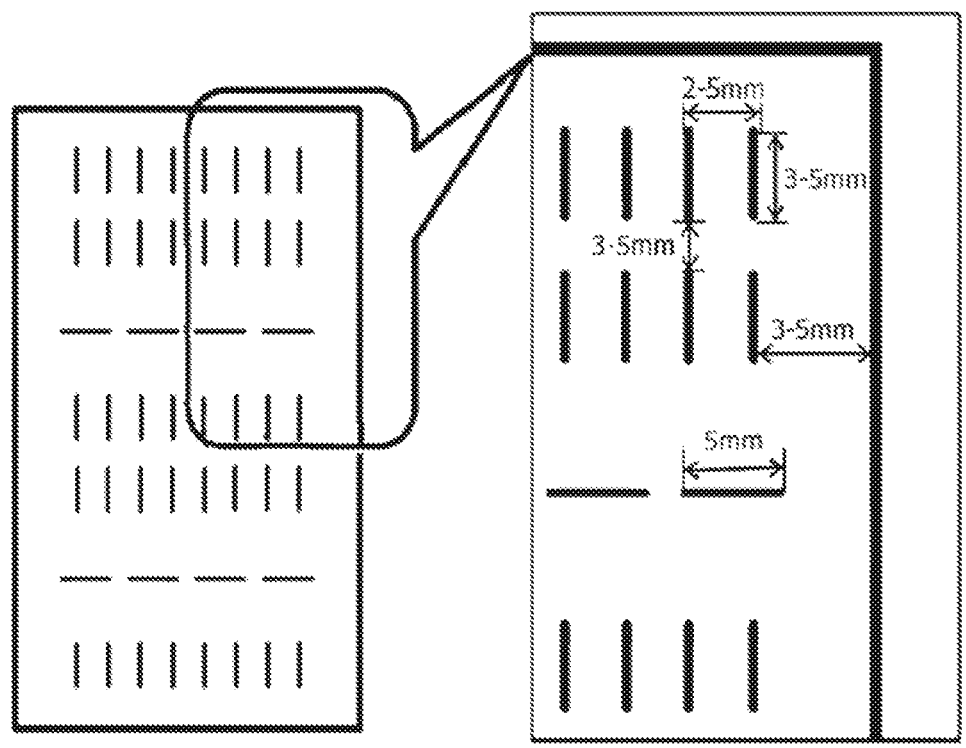
FIG. 5 is a plan view showing a graft having a multi-slit pattern according to one exemplary embodiment of the present invention.

According to one exemplary embodiment of the present invention, the multi-slit-treated graft is shown in FIGS. 1, 4 and 5, but the present invention is not limited thereto.

In the present invention, a pattern of multiple slits may be formed with longitudinal lines, transverse lines, Y, V, and Z shapes, and a combination thereof (see FIG. 4), but the present invention is not limited thereto. More particularly, the slits may be formed so that gaps between the slits range from 2 to 12 mm (preferably 2 to 5 mm) in a transverse direction, and 3 to 5 mm in a longitudinal direction, when viewed in plan. Upon formation of slits, the graft may be slit-treated so that the slits may have a length of 3 to 10 mm (preferably 3 to 5 mm) in longitudinal section and a length of 4 to 6 mm (preferably 5 mm) in transverse section. After surgery, the graft is transplanted at distances of 3 to 5 mm from edges of the graft to prevent cutting between the graft and the host tissue upon suturing (FIG. 5).

In the case of the graft formed by vertical-axis penetration of such multiple patterns of slits, extensibility of the graft in longitudinal and transverse directions may be improved to extend the graft to a tissue having the same width as the graft, thereby enabling transplantation over a wide area. Also, as an increase in flexibility of the graft expands and elongates a host tissue, the graft may be naturally elongated, thereby reducing senses of pain and inconvenience upon expansion of the graft site onto which the graft is grafted.

In particular, since fine spaces of the slits provides an environment favorable for proliferation of fibroblasts, infiltration and proliferation of new blood vessels, and swift recovery of blood circulation during transplantation, the graft may be easily fused with the host tissue, and engrafted. Also, side effects such as skin necrosis, inflammation, infection, retention of bodily fluids, and formation of a capsule of scar tissue may be prevented.

Also, the multi-puncture patterns may be used without limitation as long as the multiple punctures may be formed in a circular, triangular, or quadrilateral shape with a predetermined gap. In addition, the multiple punctures may be formed between the multiple slits. Preferably, the multiple punctures have a diameter of 0.2 to 2 mm. This is so that the graft may be easily engrafted after transplantation by promoting infiltration of fibroblasts and new blood vessels. Also, a gap between the punctures is preferably in a range of 0.5 to 5 mm. This is so that the gap between the punctures may maintain the maximum physical properties of the graft.

In addition, in the case of the multi-puncture structure, a space in which an autologous tissue rapidly proliferates is formed from the host tissue surrounding the graft through the multi-penetration structure, together with the advantages achieved from the slit pattern. Penetration and proliferation of the new blood vessels into the graft may be promoted through such a space. Also, the endogenous autologous tissue proliferating through a column-shaped space serves to support and immobilize the graft itself in the host tissue, thereby preventing migration and deformation of the graft even when external stimuli such as expansion and shrinking of the host tissue around the graft, and friction of the host tissue, are applied to the graft. Also, as the newly formed autologous tissue is fused with the graft, a foreign body sensation caused by the transplantation may be reduced. In general, since the graft is inserted under the subcutaneous tissue, blood supply into the subcutaneous tissue and the skin positioned on the graft may be reduced upon transplantation due to the volume enlargement of the inserted graft. As a result, oppressive necrosis may be easily caused due to low blood supply. According to the present invention, however, since rapid formation of new blood vessels may be induced at a site in direct contact with host tissue lined under the graft through the plurality of column-shaped spaces, the blood supply into the subcutaneous tissue and the skin increases, thereby preventing ischemic necrosis caused by a decrease in blood flow into the subcutaneous tissue and the skin. Also, lost connections between the host tissues by insertion of the graft may be rapidly repaired to connect bodily fluid circulation including blood circulation between the tissues through the porous structure together with the multiple slits, and to inhibit retention of bodily fluids, thereby preventing formation of a dead space and a capsule of scar tissue between the graft and the host tissue, and reducing the tendency for inflammation and infection.

For example, when the graft is applied to a penile enhancement surgery in the department of urology, the graft serves as a support by inducing rapid infiltration and proliferation of autologous tissue from the Dartos fascia and Buck's fascia of both surfaces of the graft at a penetration site, thereby preventing migration or deformation of the graft by physical stimuli such as sexual activity, etc.

Figure 6:
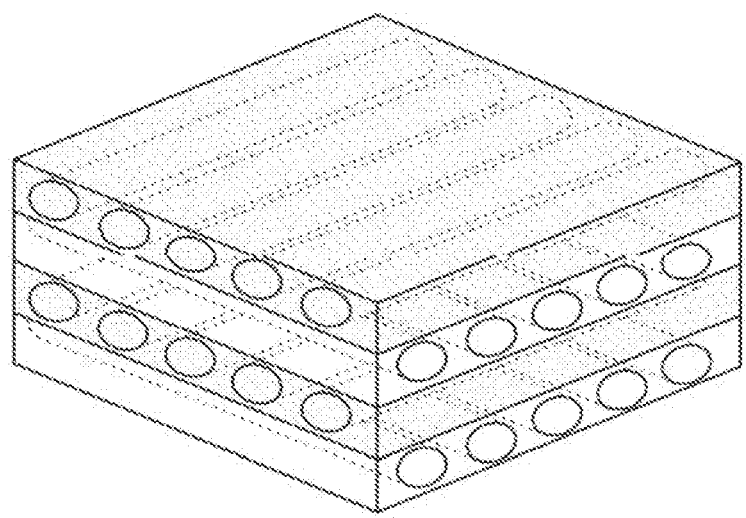
FIG. 6 is a perspective view showing a graft having an alternately stacked, horizontal-axis multi-penetration shape.

Also, the alternately stacked horizontal-axis multi-penetration shape refers to an alternately stacked penetration structure in which one layer is penetrated several times along a longitudinal line and another layer is penetrated several times along a transverse line. As shown in FIG. 6, one layer having a transversally aligned penetration structure is stacked on another layer having a longitudinally aligned penetration structure, which is referred to as an alternately stacked structure. Since such a stacked structure provides flexibility to the graft in both longitudinal and transverse directions, extensibility of the graft may be improved when the graft is immobilized in a host tissue upon transplantation. As a result, surgery may be easily performed, a foreign body sensation may be lowered after surgery, and pain may be relieved. Also, since proliferation and penetration of new blood vessels in the host tissue are promoted after transplantation, a more favorable transplantation environment may be provided, in which proliferation of fibroblasts is promoted to enhance proliferation of an endogenous collagen tissue. In addition, since a grafting rate of the graft is increased while facilitating proliferation of autologous tissues, it is possible to induce successful transplantation. Further, hydration of the graft required to provide for transplantation of the graft may be more easily performed. In this case, the entire graft may be uniformly hydrated. Also, a foreign body sensation which patients feel after the graft transplantation is often caused since the graft itself generally does not induce a biocompatible graft response with the host tissue. However, since the transplantation environment has an optimized structure through the horizontal-axis multi-penetration shape as described above, the sense of foreign body may be significantly relieved after the transplantation. In this case, the penetration site may have a penetration diameter (size) of 0.2 to 0.5 mm. A gap between the penetrations may be in a range of 0.3 to 3 mm.

Also, the graft according to one exemplary embodiment of the present invention may have corner portions slope-cut therein.

Figure 10:
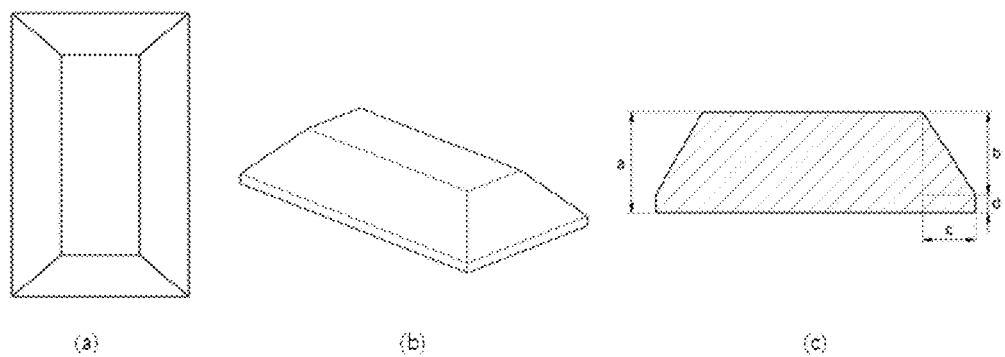
FIG. 10 is a plan view (a), a perspective view (b) and a cross-sectional view (c) of the acellular dermal graft having corners slope-cut therein.

The expression "corner portion having slope cut therein" refers to a state in which corners of the top surface of a quadrilateral graft (segments forming boundaries between surfaces in a polyhedron) are properly treated to form slopes. Also, at least one (1 to 4) corner of the top surface of the graft may be subjected to slope cutting. After the slope cutting, a bottom side of the slope may have a length of 5 to 10 mm (FIG. 10(c)-c), and the graft which is not slope-cut even after the slope cutting may have a height of 1 to 2 mm (FIG. 10(c)-d). In particular, the height (FIG. 10(c)-b) of the slope-cut slope may account for at least 60% (preferably 65 to 85%) of the height (FIG. 10(c)-a) of the graft before the slope cutting. This is because the height has a smooth external appearance after the transplantation, and minimizing contact between a stitching fiber and the graft upon suturing the host tissue may reduce an inflammatory response.

Figure 2:
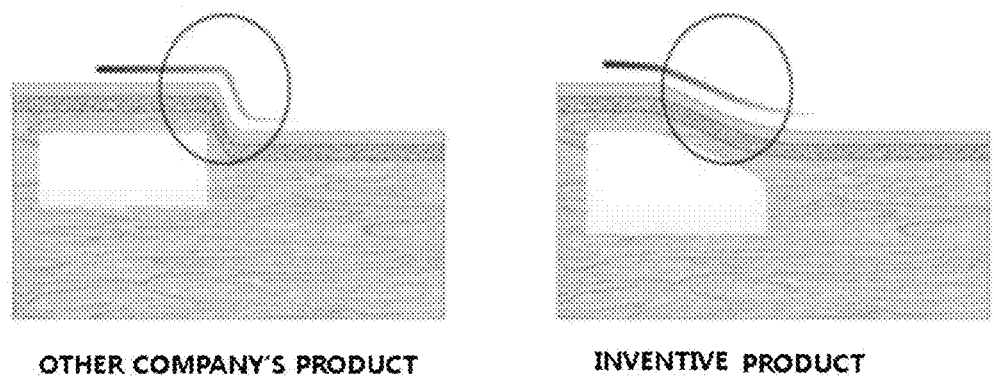
FIG. 2 is a diagram showing results obtained by comparing an acellular dermal graft (with corners subjected to slope cutting) according to one exemplary embodiment of the present invention with a conventional acellular dermal graft (Alloderm®, LifeCell Corporation, Branchburg, N.J.).

As shown in FIG. 2, in the case of an established acellular dermal graft (Alloderm®, LifeCell Corporation, Branchburg, N.J.), since corner portions of the graft are not slope-cut, skin at the graft site protrudes after transplantation when the untreated graft itself is used for transplantation, which gives the graft an unnatural appearance. On the other hand, the graft according to the present invention has an advantage in that skin at the graft site does not protrude after the transplantation since corner portions of a quadrilateral acellular dermal tissue for transplantation are slope-cut, thereby maintaining a smooth external appearance of the graft. Also, when a sutured site of the graft is immobilized in the host tissue using a stitching fiber, the graft is immobilized in the host tissue by passing a stitching fiber through parts of edges of the slope-cut slope rather than suturing the entire graft in a thickness direction. Therefore, contact between the stitching fiber and the graft may be minimized, thereby reducing the tendency for inflammation.

Also, the graft according to one exemplary embodiment of the present invention may be a graft from which a basement membrane layer is removed.

A skin tissue of a human body is composed of the outermost epidermis, a dermis, and a subcutaneous tissue. In general, the epidermis is removed during formation of the graft using a human dermal tissue, and a basement membrane layer serving to bind the dermis to the epidermis is positioned on the dermis in a state in which the dermis remains on the graft. The basement membrane layer has a histologically compact structure, and thus serves to structurally support a dermal tissue graft. However, such a compact structure is unfavorable for penetration of new blood vessels from the host tissue, formation and migration of fibroblasts, etc. Therefore, since the graft is not transplanted due to poor grafting of the host tissue with a surface of the graft from which the basement membrane layer is not removed, a space may be formed, or a capsule of scar tissue may be generated, which leads to retention of bodily fluid.

Figure 3:
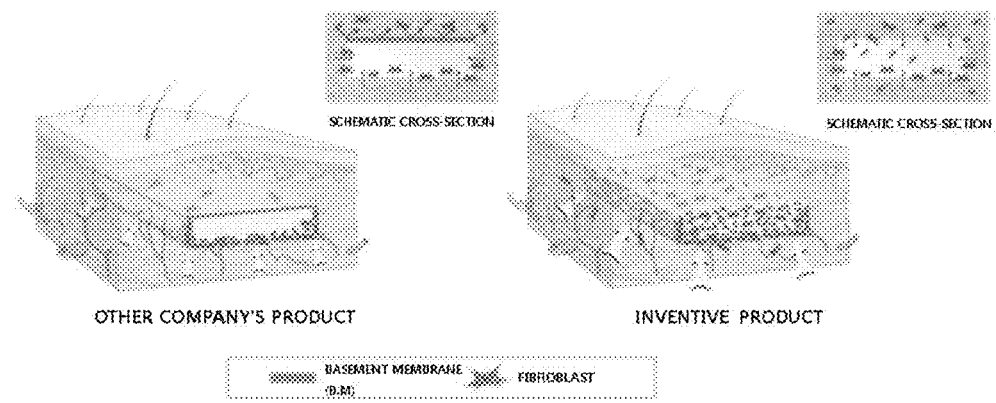
FIG. 3 is a diagram showing results obtained by comparing an acellula dermal graft (with basement membrane layer removed therefrom) according to one exemplary embodiment of the present invention with a conventional acellular dermal graft (Alloderm®, LifeCell Corporation, Branchburg, N.J.).

As shown in FIG. 3, in the case of the established acellular dermal graft (Alloderm®, LifeCell Corporation, Branchburg, N.J.), since a basement membrane layer is positioned on an upper portion of the dermis, the uptake of fibroblasts in a preexisting graft site is prevented after transplantation. As a result, a grafting rate of the graft onto the skin may be drastically reduced at sites of a lateral portion and a lower end of the dermis from which the basement membrane layer is removed. To solve these prior-art problems, the graft according to one exemplary embodiment of the present invention may be used to significantly enhance the uptake of fibroblasts in a preexisting graft site by removing a basement membrane layer, compared with conventional dermal tissue grafts, and to promote formation of new blood vessels to improve a grafting rate of the graft onto the skin.

When the entire basement membrane layer is removed, solidity of the graft degraded, it may be difficult to perform suturing required to immobilize the graft in the host tissue, and an immobilization effect may be lost since the graft is easily torn by formation of tension.

Removal of the entire basement membrane may degrade solidity of the graft, make it difficult to perform suturing required to immobilize the graft in the host tissue, and lose an immobilization effect since the graft is easily torn by formation of tension.

Especially, to immobilize the graft in the host tissue, a basement membrane layer of the graft may be partially removed while leaving the basement membrane layer intact at a site which is sutured with the host tissue. When the basement membrane layer is left intact in the sutured site, the graft may be readily immobilized in the host tissue in spite of tension caused by firmness of the basement membrane layer, thereby preventing migration and deformation of the graft. Also, uptake and proliferation of fibroblasts from the host tissue toward the graft upon biding to the host tissue may be rapidly promoted in the other site of the graft rather than the sutured site by removing the basement membrane layer, and formation and penetration of new blood vessels may be promoted to facilitate binding between the host tissue and the graft, thereby preventing formation of dead space and retention of bodily fluid. As a result, it is possible to inhibit side effects caused after surgery and to facilitate rapid transplantation and recovery.

Figure 9:
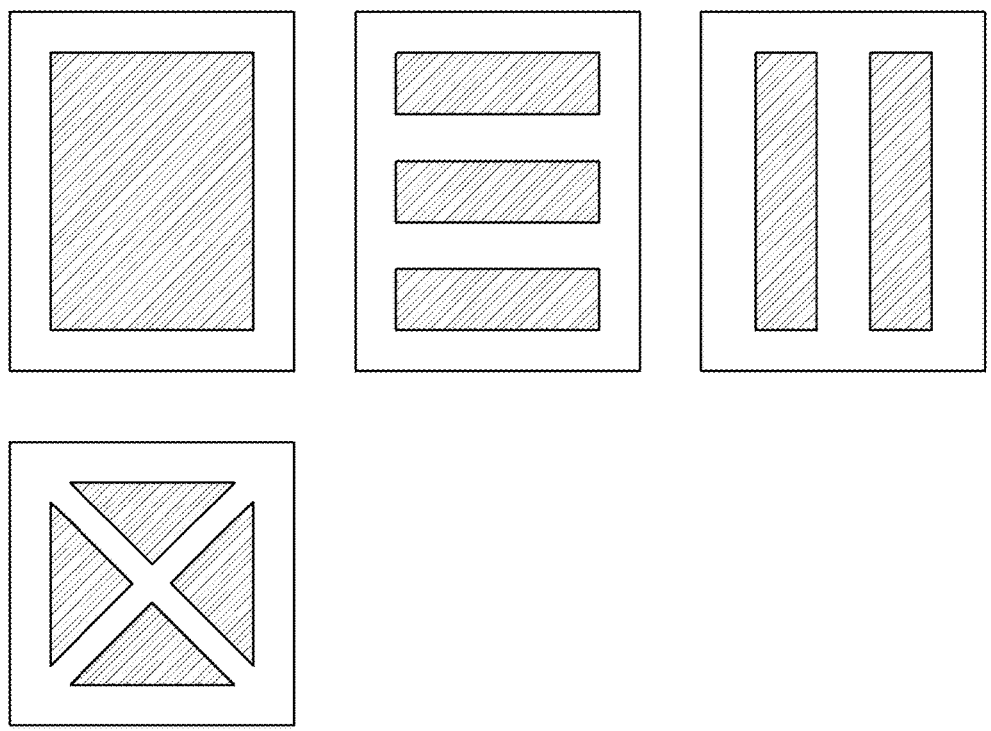
FIG. 9 is a plan view of an acellular dermal graft in which a part of a basement membrane layer is removed in various shapes (slashed region: basement membrane layer-removed region; white region: suture region between a host tissue and the graft, and region in which a basement membrane layer remains).

FIG. 9 shows grafts having various shapes in which a region to be sutured is left a basement membrane layer intact.

The present invention is also directed to providing a method of preparing an acellular dermal graft. Here, the method includes:
 forming multiple penetrations.

More particularly, the method according to one exemplary embodiment of the present invention may include:
 removing an epidermis;
 removing dermal cells;
 forming multiple penetrations; and
 performing cryopreservation.

In addition, the present invention is directed to providing a method of preparing an acellular dermal graft. Here, the method includes:
 removing a basement membrane layer.

More particularly, the method according to one exemplary embodiment of the present
 invention may include:
 removing an epidermis;
 removing dermal cells;
 removing a basement membrane layer; and
 performing cryopreservation.

Furthermore, the present invention is directed to providing a method of preparing an acellular dermal graft. Here, the method includes:
 slope-cutting corner portions of the graft.

More particularly, the method according to one exemplary embodiment of the present invention may include:
 removing an epidermis;
 removing dermal cells;
 performing cryopreservation; and
 slope-cutting corner portions of the graft.

Especially, the method of preparing an acellular dermal graft may include:
 removing an epidermis;
 removing dermal cells;
 removing a basement membrane layer;
 forming a multi-penetration structure;
 performing cryopreservation; and
 slope-cutting corner portions of the graft.

The method of preparing an acellular dermal graft according to the present invention will be described in further detail, as follows.

First, providing a tissue for preparing a graft may be further performed.

When tissues of a donated corpse are separated and delivered, there are risks of damage of the tissues caused by hypoxia, destruction of the tissues by autolytic enzymes, injury of an extracellular matrix by proteases, etc. Also, the tissues may be physically damaged according to an osmotic pressure of a transfer solution. In addition, there is always a risk of contamination by microorganisms such as bacteria or fungus. As a result, a compound which may prevent damage of the tissues caused by hypoxia, destruction of the tissues by autolytic enzymes, and injury of the extracellular matrix by proteases should be added to a solution used to deliver the tissues, and antibacterial agents and antifungal agents which may prevent contamination with microorganisms should be added to the solution. A suitable buffer solution should be included to prevent damage of tissues by osmotic pressure. The tissue transfer solution should have an osmotic pressure of approximately 260 to 320 mOsm/kg, which is substantially the same as an osmotic pressure of blood plasma. A commercially available medium widely used for an animal cell culture has an osmotic pressure of approximately 260 to 320 mOsm/kg, which is similar to an osmotic pressure of blood plasma. Therefore, the commercially available medium may be used as a basic solution, and may be also used after a component having various functions is added thereto.

To prevent contamination by bacteria or mold, antibacterial agents such as penicillin, streptomycin, kanamycin, neomycin, bacitracin, gentamicin, polymyxins or vancomycin may be used alone or in combination, and antifungal agents such as amphotericin B, nystatin, may be used alone or in combination. To prevent damage of the tissues by various decomposition enzymes, an enzyme inhibitor should also be added.

The enzyme inhibitors that may be used herein may include a chelating agents such as N-ethyl maleimide (NEM), phenylmethylsulfonyl fluoride (PMSF), ethylenediaminetetraacetic acid (EDTA), or ethylene glycol-bis(2-aminoethylo)-N,N,N',N'-tetraacetic acid (EGTA), a protease inhibitor such as chelating compound, leupeptin, or apoprotein, etc.

In addition, the tissues should be delivered according to a method capable of minimizing physical damage of the tissues.

Most enzymatic reactions are highly affected by a change in temperature, and exhibit the strongest enzymatic activities at approximately 37° C., which is human body temperature. Therefore, the tissues are delivered at a low temperature of approximately 4° C.

In general, the tissues may be delivered in an icebox filled with ice. When the tissues are delivered at a low temperature at which a transfer solution is likely to be frozen, ice crystals may cause damage to the tissues.

The next operation is to remove the epidermis from the tissue prepared as described above. Here, the epidermis and the dermis are separated.

In general, various proteases may be used to separate the dermis and the epidermis. When an enzyme is used at a low concentration or treated for a very short treatment time, the epidermis and the dermis are not easily separated. On the other hand, when the enzyme is used at a high concentration or for an excessively long treatment time, damage of cells or tissues may be caused. Therefore, the tissues should be treated with the enzyme at a suitable concentration for a suitable treatment time. The enzyme used to separate the dermis and the epidermis may include a neutral protease such as dispase, hermolysin, trypsin, etc. When the tissue is treated with dispase at a concentration of 1.0 units/ml and a temperature of 37° C. for 60 to 120 minutes, the dermis and the epidermis may be separated. Also, when the tissue is treated with hermolysin at a concentration of 200 µg/ml and a temperature of 37° C. for 30 minutes, the dermis and the epidermis may be separated. The use of hermolysin may reduce damage of the basement membrane, compared with the use of dispase. An alternative method is to separate two layers of the tissue by varying an ionic strength of a solution. In this method, grafting efficiency varies according to the conditions such as ionic strength, treatment time, and treatment temperature. When the tissue is treated with 1 mole or more of a sodium chloride solution at 37° C. for 14 to 32 hours, the dermis and the epidermis may be separated. Since bacteria and mold do not grow in 1 mole or more of sodium chloride solution, use of the sodium chloride solution may reduce a risk of contaminating the graft with microorganisms. Also, even when the tissue is treated with a 20 mM ethylenediaminetetraacetic acid (EDTA) solution at 37° C. for 14 to 32 hours, the dermis and the epidermis may still be separated. The use of EDTA may reduce damage of the tissues caused by proteases since the EDTA serves as a protease inhibitor. When the tissue is treated with a 1 mole sodium chloride solution to which 1 to 5 mM EDTA is added, contamination with microorganisms and damage of the tissues by an enzyme may be minimized, and the dermis and the epidermis may be separated.

The next operation is to remove the epidermis, followed by removing the dermal cells, as described above.

Membrane proteins present in a cell membrane mainly initiate an immune response. Therefore, removal of the cells may minimize the membrane protein. In the present invention, a method of selectively removing only cells without damage of tissues using a difference in physical and chemical properties between the cells and an extracellular matrix may be used. Since main ingredients of the cell membrane are phospholipids, the cells may be removed without damage of the tissues using various surfactants.

For this purpose, an ionic surfactant such as sodium dodecyl sulfate (SDS), or a nonionic surfactant such as Triton X-100, Tween 20, Tween 40, Tween 60, Tween 80, Nonidet P-10 (NP-10), or Nonidet P-40 (NP-40) may be used.

When the dermis is treated with a 0.2 to 1% SDS solution at room temperature for 30 to 120 minutes, the cells may be removed without damage of the tissues. Also, when the dermis is treated with a 0.1 to 2.0% Tween 20 solution at room temperature for 30 to 180 minutes, or treated with a 0.2 to 2% Triton X-100 or Nonidet P-40 solution at a temperature of 22 to 37° C. for 30 to 180 minutes, the cells may be removed without damage of the tissues.

In addition to the chemical methods, the cells may also be removed using a physical method. That is, when the dermis is treated for 5 to 60 minutes using ultrasonic waves having a frequency of 10 to 100 kHz, the cells may be removed.

Also, the cells may also be removed without damage of the tissues using a combination of a surfactant and ultrasonic waves.

In addition, a solvent (TNBP) and a surfactant may be used to remove the cells and virus at the same time.

The next operation is to further remove cells from the dermis, followed by removing a basement membrane layer. When the basement membrane is removed, uptake of the fibroblasts may be enhanced, and angiogenic activities may be improved. As a result, transplantation may be more stably performed due to an increase in grafting reaction with the host tissue.

A method of separating a basement membrane layer from a dermal tissue may include a physical method, and a chemical method using a chemical compound which is not harmless to human bodies. The physical method is a method of cutting an upper surface of the epidermis-free dermis into slices having a small thickness of 0.01 to 0.5 mm (preferably 0.05 to 0.2 mm) using a tissue cutting machine. In this case, blades of the tissue cutting machine may be formed of carbon steel so as to minimize generation of heat to prevent deformation of the dermal tissue. The chemical treatment method is a method capable of removing a basement membrane without damage of the dermal tissue by forming fine holes in an upper surface of a basement membrane layer using a roller provided with fine needles, and treating the basement membrane layer with a 0.3% oxygenated water solution for approximately 1 to 3 hours so as to separate the basement membrane layer from the dermis. By removing the basement membrane layer, the uptake of the fibroblast in a preexisting graft site may be significantly enhanced compared to the conventional dermal tissue graft and formation of new blood vessels may be promoted, thereby improving a grafting reaction with the host tissue. In this case, it should be noted that it is more desirable not to remove the basement membrane layer which may provide a site for the graft to be sutured with the host tissue after transplantation.

The next operation is to further form a multi-penetration structure.

Particularly, the multi-penetration structure includes a vertical-axis multi-penetration structure and/or an alternately stacked horizontal-axis multi-penetration structure. In the vertical-axis multi-penetration structure, penetrations are formed from an upper surface to a bottom surface of the graft. In this case, a penetration pattern may be a multi-slit pattern and/or a multi-puncture pattern.

The vertical-axis multi-penetration structure and the horizontal-axis multi-penetration structure may be formed in various patterns, as described above.

A method of forming the vertical-axis and horizontal-axis penetration structures will be described in further detail, as follows.

The multi-slit pattern may be manually formed using a blade, or a device capable of forming multiple slits (for example, a multi-cutting blade, a skin mesher, etc.). Also, the multi-puncture pattern may be formed by immobilizing corner portions of the dermis using a multiple needle layer and performing vertical-axis penetration on the dermis in one direction. In the case of the horizontal-axis penetration pattern, the multiple penetrations may be formed while maintaining a horizontal angle by performing multiple penetrations on one layer in one direction, followed by performing multiple penetrations on a lateral side of another layer next to the one layer. In this case, when the horizontal angle of the lateral side is maintained to encroach on an underlying layer in a penetration direction, physical properties of the tissue may not be maintained. As a result, great care should be exercised to avoid twisting of a shape of a product after lyophilization.

The next operation is to preserve the graft by treating the graft with a freezing solution and lyophilizing the graft.

The freezing solution was composed of a buffer solution for maintain an ionic strength or osmotic pressure of a solution, a cryoprotectant for preventing physical and chemical damage of a dermis tissue upon freezing, and a drying protective agent for preventing a change in structure of the dermis tissue upon drying. The cryoprotectant serves to enhance stability of a frozen tissue by increasing a glass transition temperature. When the glass transition temperature increases, a drying rate may be further enhanced by increasing an amount of vitreous ice or square ice which is less stable than hexagonal ice in the tissue. Also, the vitreous ice and square ice cause less damage of the tissue since the vitreous ice and square ice have a small ice crystal size. As a result, the cryoprotectant may be essentially included in the freezing solution. The cryoprotectant widely used so far may include dimethyl sulfoxide (DMSO), dextran, sugar, propylene glycol, glycerol, mannitol, sorbitol, fructose, trehalose, raffinose, 2,3-butanediol, hydroxyethyl starch (HES), polyethylene glycol, polyvinylpyrrolidone (PVP), proline, hetastarch, serum albumin, etc. A combination of these components and various base components are used to prepare a freezing solution. Among these, dextran, glycerol, hetastarch, mannitol, and hydroxyethyl starch may be used as a serum replacement. Also, polyethylene glycol may be used as a stabilizing agent for protein injections. In this aspect, stability of these components has been somewhat proven. Compounds known to be harmless to human bodies are used as main components to prepare a freezing solution. The dermis is dipped in the freezing solution prepared thus, and the freezing solution readily penetrates into the dermis using a proper method. The dermis penetrated by the freezing solution is stored in a deep freezer set to −70° C. or less (preferably −40° C. to −70° C.). After the dermis is frozen for 12 to 48 hours, the dermis may be transferred to a freeze dryer and lyophilized for 24 to 50 hours.

The next operation involves further cryopreserving the dermal tissue, followed by slope-cutting corner portions of the dermal tissue.

More particularly, corners of a top surface of a quadrilateral graft are properly treated to form slopes. In this case, at least one corner of the top surface of the graft may be subjected to slope cutting. A specific slope cutting process is as described above. Also, a surface of the graft which is not subjected to the slope cutting should be a site in which the basement membrane layer remains intact. In the slope cutting process, a lateral surface of the dermal tissue is cut using an ultrasonic cutter, which does not generate heat in the dermal tissue, in a state in which the acellular dermal graft is immobilized in a jig. Also, the corner portions may be cut with various patterns such as a wave pattern, a sawtooth pattern, a flat pattern, etc.

The acellular dermal graft prepared thus may be used as a therapeutic agent for treating injuries of the skin including restoration of injured tissues, plastic operation, enlargement, filling, tissue protection, etc.

That is, the acellular derma graft according to one exemplary embodiment of the present invention may be used as a skin restoring agent for restoring injured skin caused by burns, traffic accidents and sores, a full-thickness skin reconstructing agent, a septum reconstructing agent, a reconstructing agent for avulsion injuries of craniospinal dura mater, a depression correcting agent, a scar correcting agent, and a hemifacial atrophy correcting agent in the fields of dermatology, plastic surgery, gynecology, surgery, neurosurgery, urology, and otorhinolaryngology.

Hereinafter, the present invention will be described in further detail with reference to Examples according to the present invention and Comparative Examples which do not fall within the scope of the present invention. However, it should be understood that this detailed description is not intended to limit the scope of the present invention.

Example 1

Preparation of Acellular Dermal Graft Having Corners Slope-Cut Therein

A skin tissue (extracted from a corpse donated from the Tissue Bank for nonprofit treatment of patients) was treated with a neutral protease, dispase, at a concentration of 1.0 units/ml, stirred at a temperature of 37° C. for 60 to 120 minutes in a shaking incubator, and then washed three times with sterile distilled water to separate an epidermis and a dermis. Then, the epidermis was removed.

The resulting epidermis-free tissue was treated with a 1% Triton X-100 solution at 30° C. for 100 minutes to remove dermal cells. For the epidermis-free dermis, a 10% dextran solution was used as a freezing solution. Then, the dermal tissue was dipped in the freezing solution at −4° C. for 12 hours to promote penetration of the freezing solution, stored for 12 hours in a deep freezer with a temperature of −70° C. or less, and lyophilized for 48 hours in a freeze dryer.

Figure 11:
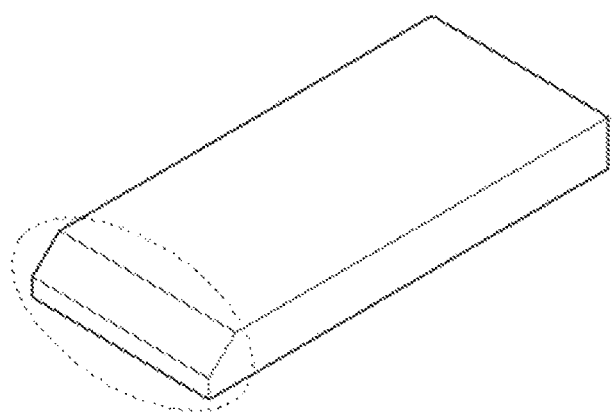
FIG. 11 is an image of the acellular dermal graft having one upper corner slope-cut therein (red dotted line: slope-cut region).

Next, corner portions of a graft (dermal tissue) having a height of 5 mm were slope-cut, as follows. The dermal tissue was subjected to slope cutting using an ultrasonic cutter, which did not generate heat in the dermal tissue, so that a bottom side of each slope had a length of 5 to 10 mm, and a portion of the slope which was not slope-cut after the slope cutting had a height of 2 mm (see FIGS. 2, 10 and 11).

Example 2

Preparation of Multi-Slit-Treated Acellular Dermal Graft

A skin tissue (extracted from a corpse donated from the Tissue Bank for nonprofit treatment of patients) was treated with a neutral protease, dispase, at a concentration of 1.0 units/ml, stirred at a temperature of 37° C. for 60 to 120 minutes in a shaking incubator, and then washed three times with sterile distilled water to separate an epidermis and a dermis. Then, the epidermis was removed.

The resulting epidermis-free tissue was treated with a 1% Triton X-100 solution at 30° C. for 100 minutes to remove dermal cells.

Figure 8:
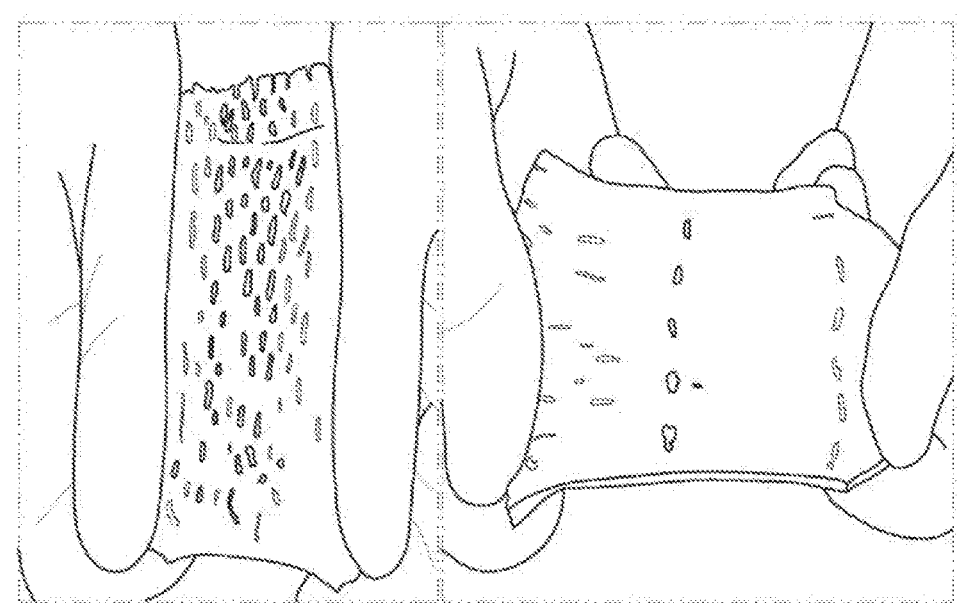
FIG. 8 is an image of an acellular dermal graft having multiple slits formed therein.

To form a multi-slit pattern on the epidermis-free dermis, a blade was used to manually perform a process of forming slits in a longitudinal or transverse direction (see FIGS. 4 and 8).

A 10% dextran solution was used as the freezing solution. Then, the dermal tissue was dipped in the freezing solution at −4° C. for 12 hours to promote penetration of the freezing solution, stored for 12 hours in a deep freezer set to −70° C. or less, and then lyophilized for 48 hours in a freeze dryer.

Next, a method of slope-cutting corner portions of a graft (dermal tissue) having a height of 5 mm was further performed, as follows. The dermal tissue was subjected to slope cutting using an ultrasonic cutter, which did not generate heat in the dermal tissue, so that a bottom side of each slope had a length of 5 to 10 mm, and a portion of the slope which was not slope-cut after the slope cutting had a height of 2 mm (see FIGS. 2, 10 and 11).

Example 3

Preparation of Vertical-Axis Circular Multi-Puncture-Treated Acellular Dermal Graft A skin tissue (extracted from a corpse donated from the Tissue Bank for nonprofit treatment of patients) was treated with a neutral protease, dispase, at a concentration of 1.0 units/ml, stirred at a temperature of 37° C. for 60 to 120 minutes in a shaking incubator, and then washed three times with sterile distilled water to separate an epidermis and a dermis. Then, the epidermis was removed.

The resulting epidermis-free tissue was treated with a 1% Triton X-100 solution at 30° C. for 100 minutes to remove dermal cells.

To form a multi-puncture pattern on the epidermis-free dermis, the dermis was immobilized in corner portions using a multiple needle layer, and penetrations were performed in vertical direction to form multiple punctures.

A 10% dextran solution was used as the freezing solution. Then, the dermal tissue was dipped in the freezing solution at −4° C. for 12 hours to promote penetration of the freezing solution, stored for 12 hours in a deep freezer set to −70° C. or less, and then lyophilized for 48 hours in a freeze dryer.

Next, a method of slope-cutting corner portions of a graft (dermal tissue) having a height of 5 mm was further performed, as follows. The dermal tissue was subjected to slope cutting using an ultrasonic cutter, which did not generate heat in the dermal tissue, so that a bottom side of each slope had a length of 5 to 10 mm, and a portion of the slope which was not slope-cut after the slope cutting had a height of 2 mm (see FIGS. 2, 10 and 11).

Example 4

Preparation of Horizontal-Axis Multi-Penetration-Treated Acellular Dermal Graft

A skin tissue (extracted from a corpse donated from the Tissue Bank for nonprofit treatment of patients) was treated with a neutral protease, dispase, at a concentration of 1.0 units/ml, stirred at a temperature of 37° C. for 60 to 120 minutes in a shaking incubator, and then washed three times with sterile distilled water to separate an epidermis and a dermis. Then, the epidermis was removed.

The resulting epidermis-free tissue was treated with a 1% Triton X-100 solution at 30° C. for 100 minutes to remove dermal cells.

Figure 7:
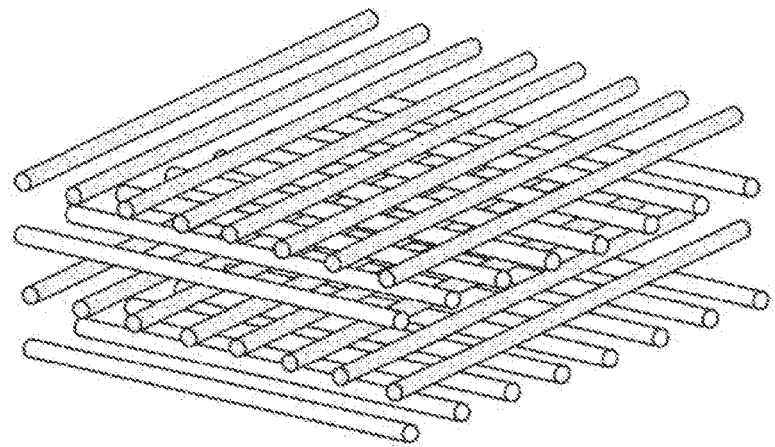
FIG. 7 is a diagram showing only a multi-penetration structure in the graft shown in FIG. 6.

To form an alternately stacked horizontal-axis multi-penetration shape on the epidermis-free dermal tissue, penetrations were performed in one direction while maintaining a horizontal angle, and penetrations in a lateral surface of another dermal tissue next to the dermal tissue were further performed to form multiple penetrations (see FIGS. 6 and 7).

A 10% dextran solution was used as the freezing solution. Then, the dermal tissue was dipped in the freezing solution at −4° C. for 12 hours to promote penetration of the freezing solution, stored for 12 hours in a deep freezer set to −70° C. or less, and then lyophilized for 48 hours in a freeze dryer.

Next, a method of slope-cutting corner portions of a graft (dermal tissue) having a height of 5 mm was further performed, as follows. The dermal tissue was subjected to slope cutting using an ultrasonic cutter, which did not generate heat in the dermal tissue, so that a bottom side of each slope had a length of 5 to 10 mm, and a portion of the slope which was not slope-cut after the slope cutting had a height of 2 mm (see FIGS. 2, 10 and 11).

Example 5

Preparation of Multidirectional Multi-Penetration-Treated Acellular Dermal Graft A skin tissue (extracted from a corpse donated from the Tissue Bank for nonprofit treatment of patients) was treated with a neutral protease, dispase, at a concentration of 1.0 units/ml, stirred at a temperature of 37° C. for 60 to 120 minutes in a shaking incubator, and then washed three times with sterile distilled water to separate an epidermis and a dermis. Then, the epidermis was removed.

The resulting epidermis-free tissue was treated with a 1% Triton X-100 solution at 30° C. for 100 minutes to remove dermal cells.

Figure 12:
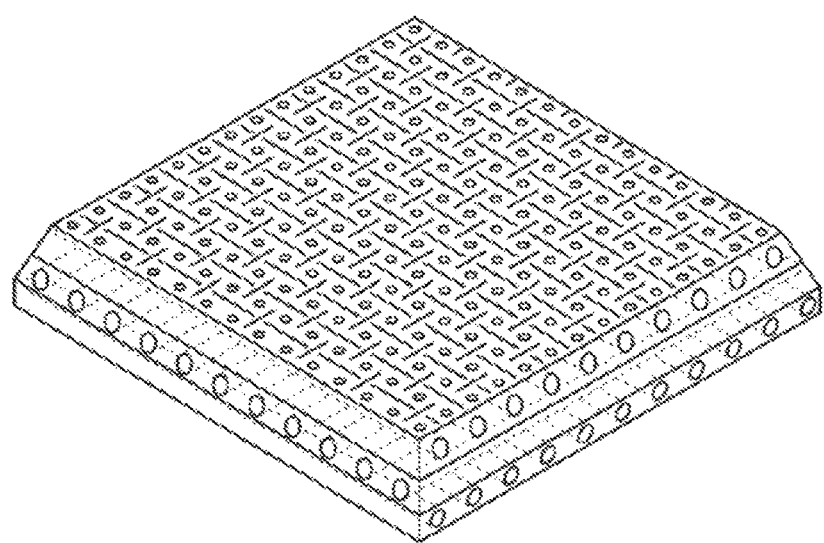
FIG. 12 is a perspective view of the acellular dermal graft according to one exemplary embodiment of the present invention.

To form an alternately stacked horizontal-axis multi-penetration shape on the epidermis-free dermal tissue, alternately stacked penetrations were formed while maintaining a horizontal angle by performing multiple transversally (left-right) aligned penetrations on one layer, followed by performing multiple longitudinally (front-rear) aligned penetrations on another layer. To form a multi-slit pattern, a blade was used to manually perform a process of forming vertically penetrating slits. Then, to form a circular multi-puncture pattern, a multiple needle layer was also used to perform a process of penetrating the dermis in one direction after immobilization of corner portions (see FIG. 12).

A 10% dextran solution was used as the freezing solution. Then, the dermal tissue was dipped in the freezing solution at −4° C. for 12 hours to promote penetration of the freezing solution, stored for 12 hours in a deep freezer set to −70° C. or less, and then lyophilized for 48 hours in a freeze dryer.

Next, a method of slope-cutting corner portions of a graft (dermal tissue) having a height of 5 mm was further performed, as follows. The dermal tissue was subjected to slope cutting using an ultrasonic cutter, which did not generate heat in the dermal tissue, so that a bottom side of each slope had a length of 5 to 10 mm, and a portion of the slope which was not slope-cut after the slope cutting had a height of 2 mm (see FIGS. 2, 10 and 11).

Example 6

Preparation of Acellular Dermal Graft from which a Basement Membrane Layer is Removed A skin tissue (extracted from a corpse donated from the Tissue Bank for nonprofit treatment of patients) was treated with a neutral protease, dispase, at a concentration of 1.0 units/ml, stirred at a temperature of 37° C. for 60 to 120 minutes in a shaking incubator, and then washed three times with sterile distilled water to separate an epidermis and a dermis. Then, the epidermis was removed.

The resulting epidermis-free tissue was treated with a 1% Triton X-100 solution at 30° C. for 100 minutes to remove dermal cells.

A basement membrane layer was removed by cutting an upper surface of the epidermis-free dermis into slices having a small thickness of 0.05 to 0.2 mm using a tissue cutting machine with blades made of carbon steel so as to minimize generation of heat to prevent deformation of a dermal tissue.

A 10% dextran solution was used as the freezing solution. Then, the dermal tissue from which the basement membrane layer was removed was dipped in the freezing solution at −4° C. for 12 hours to promote penetration of the freezing solution, stored for 12 hours in a deep freezer set to −70° C. or less, and then lyophilized for 48 hours in a freeze dryer.

Example 7

Preparation of Acellular Dermal Graft from which a Basement Membrane Layer is Partially Removed A skin tissue (extracted from a corpse donated from the Tissue Bank for nonprofit treatment of patients) was treated with a neutral protease, dispase, at a concentration of 1.0 units/ml, stirred at a temperature of 37° C. for 60 to 120 minutes in a shaking incubator, and then washed three times with sterile distilled water to separate an epidermis and a dermis. Then, the epidermis was removed.

The resulting epidermis-free tissue was treated with a 1% Triton X-100 solution at 30° C. for 100 minutes to remove dermal cells.

As shown in the first panel of FIG. 9, the basement membrane layer remaining except the site (an edge region left with an size of approximately 2 to 5 mm) to be sutured with the host tissue was removed by cutting the epidermis-free dermis into slices having a small thickness of 0.05 to 0.2 mm using a tissue cutting machine with blades made of carbon steel.

A 10% dextran solution was used as the freezing solution. Then, the dermal tissue from which the basement membrane layer was partially removed was dipped in the freezing solution at −4° C. for 12 hours to promote penetration of the freezing solution, stored for 12 hours in a deep freezer set to −70° C. or less, and then lyophilized for 48 hours in a freeze dryer.

Example 8

Preparation of Acellular Dermal Graft

A skin tissue (extracted from a corpse donated from the Tissue Bank for nonprofit treatment of patients) was treated with a neutral protease, dispase, at a concentration of 1.0 units/ml, stirred at a temperature of 37° C. for 60 to 120 minutes in a shaking incubator, and then washed three times with sterile distilled water to separate an epidermis and a dermis. Then, the epidermis was removed.

The resulting epidermis-free tissue was treated with a 1% Triton X-100 solution at 30° C. for 100 minutes to remove dermal cells.

As shown in the first panel of FIG. 9, the basement membrane layer remaining except the site (an edge region left with an size of approximately 2 to 5 mm) to be sutured with the host tissue was removed by cutting the epidermis-free dermis into slices having a small thickness of 0.05 to 0.2 mm using a tissue cutting machine with blades made of carbon steel.

To form an alternately stacked horizontal-axis multi-penetration shape on the dermis from which the basement membrane layer was partially removed, alternately stacked penetrations were formed while maintaining a horizontal angle by performing multiple transversally (left-right) aligned penetrations on one layer, followed by performing multiple longitudinally (front-rear) aligned penetrations on another layer.

To form a multi-slit pattern, a blade was used to manually perform a process of forming vertically penetrating slits. Then, to form a multi-puncture pattern, a multiple needle layer was also used to perform a process of penetrating the dermis in one direction after immobilization of corner portions (see FIG. 12).

A 10% dextran solution was used as the freezing solution. Then, the dermal tissue was dipped in the freezing solution at −4° C. for 12 hours to promote penetration of the freezing solution, stored for 12 hours in a deep freezer set to −70° C. or less, and then lyophilized for 48 hours in a freeze dryer.

Next, corner portions of a graft (dermal tissue) having a height of 5 mm were slope-cut, as follows. The dermal tissue was subjected to slope cutting using an ultrasonic cutter, which did not generate heat in the dermal tissue, so that a bottom side of each slope had a length (FIG. 10(c)-c) of 5 to 10 mm after the slope cutting, and a portion of the graft which was not slope-cut after the slope cutting had a height (FIG. 10(c)-d) of 2 mm (see FIG. 12).

Experimental Example 1

Confirmation of Proliferation of Autologous Tissue

The multi-slit-treated acellular dermal graft prepared in Example 2 was cut into slices having a size of 1×1 cm$^2$, and dipped in a Dulbecco's modified eagle's medium (DMEM) for 20 minutes. Thereafter, the previously prepared fibroblasts were inoculated at a density of 1×10$^6$/30 μl in the graft, and adhered for 5 hours in a 37° C. incubator. Then, a culture broth was carefully put into the incubator to prevent detachment of the cells, so that the graft in which the cells were inoculated was immersed in the culture broth, and the cells were cultured for 3 days in a submerged state.

The acellular dermal graft of Example 2 cultured for 3 days was immobilized with 10% formalin, stained with hematoxylin and eosin, and then observed to determine whether the cells were three-dimensionally cultured over the graft.

For comparison, a conventional acellular dermal graft (Alloderm®, LifeCell Corporation, Branchburg, N.J.) was tested in the same manner as described above.

Figure 13:
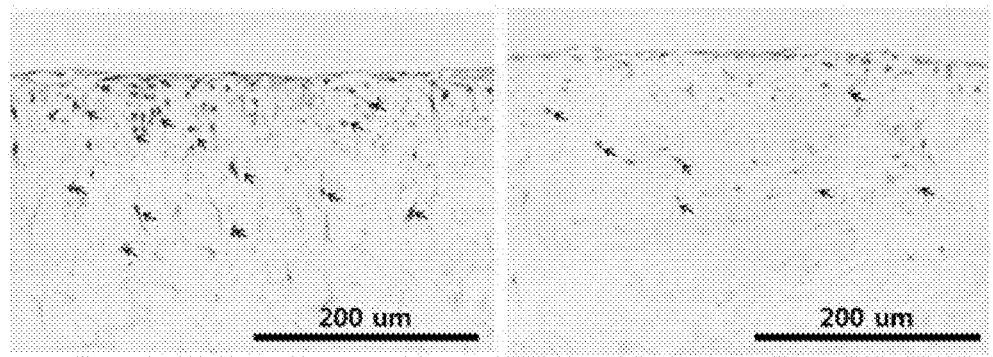
FIG. 13 is an image of the acellular dermal tissue that is stained with hematoxylin and eosin 3 days after culture of fibroblasts (Left: acellular dermal graft prepared in Example 2; Right: conventional acellular dermal graft; and black arrow: fibroblasts stained with hematoxylin).

As a result, it could be seen that the fibroblasts were highly migrated and engrafted in the peripheries of the acellular dermal graft prepared in Example 2, as shown in FIG. 13 (black arrows in a left panel of FIG. 13). On the other hand, in the case of the conventional acellular dermal graft, it could be seen that the fibroblasts were less infiltrated into the graft, compared with the acellular dermal graft prepared in Example 2 (black arrows of a right panel of FIG. 13).

Experimental Example 2

Confirmation of Uptake of Fibroblasts

A Sprague Dawley rat weighing 180 g was anesthetized using Rompun. After the anesthesia, the back of the rat was shaved using clippers, and tissues having a size of 1×1 cm$^2$ were transplanted in both sides of the back of the rat. In this case, the conventional acellular dermal graft and the acellular dermal graft prepared in Example 5 were transplanted in the right and left sides, respectively. A transplantation method was performed by incising a tissue with a size of approximately 5 mm with a blade, subcutaneously inserting a graft and suturing the tissue. After the suturing, the rat was treated with povidone-iodine to come out of the anesthesia, and then transferred to a breeding farm.

Four weeks after the transplantation, the transplanted acellular dermal tissues were taken together with skin tissues for a tissue test. This method was performed by allowing 100 ml of a saline solution, and then 500 ml of a 10% formalin solution (a fixative) prepared using a phosphate buffer to flow to the heart of a laboratory animal. First, 200 ml of a fixing solution was allowed to flow for 5 minutes, 300 ml of the remaining fixing solution was allowed to flow for 25 minutes, and a tissue was extracted and then immobilized in a fixing solution for 3 hours. Next, the tissue was dipped in a phosphate buffered saline (PBS) supplemented with 30% sucrose, and stored at 4° C. for a day. The next day, the extracted skin tissue was quickly frozen, and sliced into pieces having a thickness of 30 µm. Then, the skin tissue was stained with hematoxylin and eosin, and observed to determine uptake of fibroblasts and formation of new blood vessels and confirm a skin grafting rate.

Figure 14:
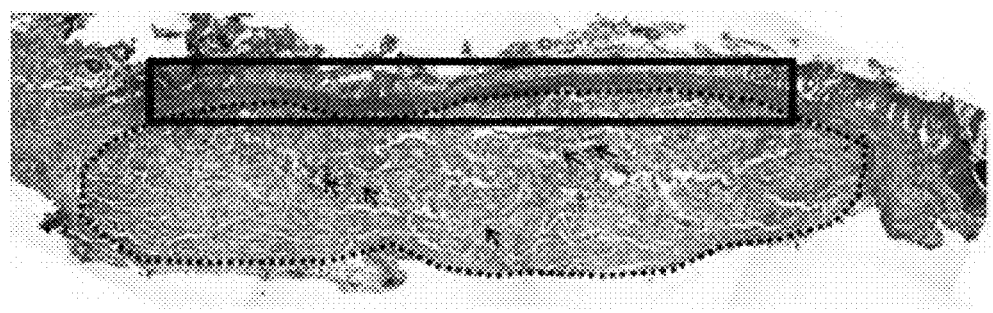
FIG. 14 is an image of the conventional acellular dermal graft after transplantation (black thick solid line: basement membrane layer and fibroblasts accumulated without penetrating into a dermal tissue graft by the basement membrane layer; black dotted line: transplanted acellular dermal tissue; and black arrow: engrafted fibroblast).
Figure 15:
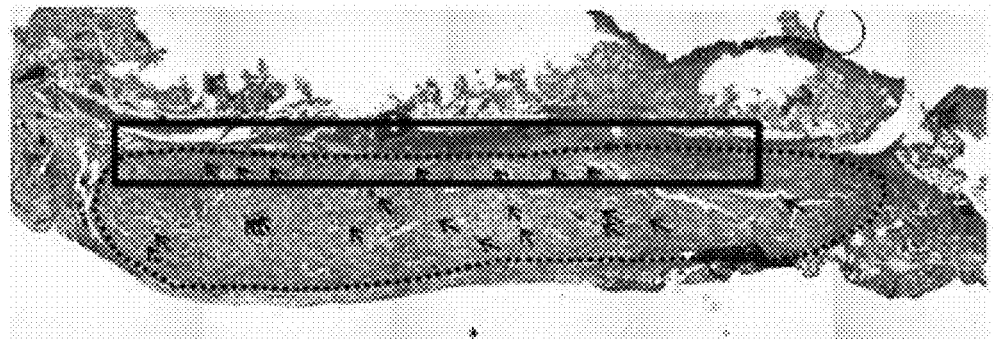
FIG. 15 is an image of the acellular dermal graft of Example 5 after transplantation (black thick solid line: the side which the basement membrane layer was removed; black dotted line: transplanted acellular dermal tissue; and black arrow: engrafted fibroblast).

As shown in FIGS. 14 and 15, it could be seen that, when the conventional acellular dermal graft was stained with hematoxylin, a marker capable of determining the presence of fibroblasts, the fibroblasts in the basement membrane layer were not taken up under the basement membrane layer, but gathered on the basement membrane layer (black arrows in FIG. 14). On the other hand, it was confirmed that, since the basement membrane layer was removed in the case of the graft prepared in Example 5, the fibroblasts did not gather on an upper side, but were uniformly engrafted over the graft (black arrows in FIG. 15).

Experimental Example 3

Confirmation of Formation of New Blood Vessels

The acellular dermal tissue transplanted in the same manner as in Experimental Example 2 was stained with hematoxylin and eosin to determine whether new blood vessels were formed on the graft.

Figure 16:
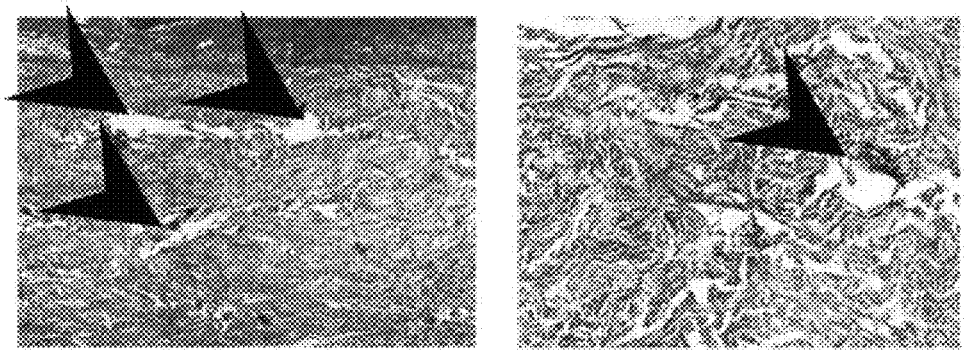
FIG. 16 is an image of the transplanted acellular dermal tissue in which formation of blood vessels is confirmed (Left: acellular dermal graft prepared in Example 5; Right: conventional acellular dermal graft; and black arrow: newly formed blood vessels).

As shown in FIG. 16, it could be seen that a larger amount of blood vessels were newly formed on the graft prepared in Example 5, compared with the conventional acellular dermal graft (black arrows).

Experimental Example 4

Confirmation of Skin Grafting Rate

The acellular dermal tissue transplanted in the same manner as in Experimental Example 2 was stained with hematoxylin and eosin to determine a skin grafting rate of the graft.

Figure 17:
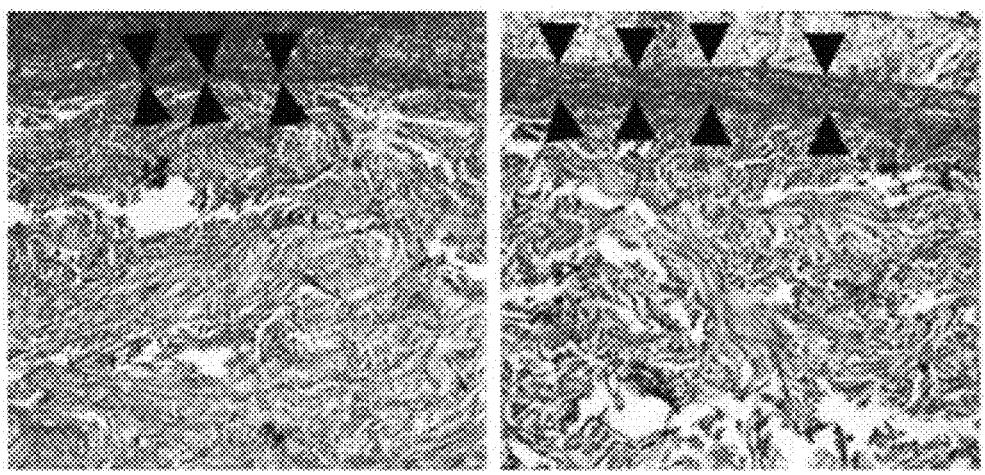
FIG. 17 is an image of the transplanted acellular dermal tissue in which a skin grafting rate is confirmed (Left: acellular dermal graft prepared in Example 5; and Right: conventional acellular dermal graft).

As shown in FIG. 17, it could be seen that the fibroblasts on the basement membrane layer did not penetrate into the graft, and were deposited on the graft due to the presence of the basement membrane layer in the case of the conventional acellular dermal tissue. On the other hand, it could be seen that the fibroblasts infiltrated into the graft and grew in the case of the acellular dermal tissue of Example 5 from which the basement membrane layer was removed. As a result, it was confirmed that a larger number of fibroblasts grew on the acellular dermal graft from which the basement membrane layer was removed.

Experimental Example 5

Cell Infiltration and Fibroblast Activation

The graft of Example 2 having a multi-slit structure formed therein was doubly stained with DAPI and fibronectine to determine cell infiltration and activation of fibroblasts.

A DAPI image was used as a cell marker (DNA staining in live cells) upon fluorescence staining, and the fibronectin was a marker which took part in adhesion, growth and migration of cells and showed that fibroblasts were activated.

The graft of Example 2 having a multi-slit structure formed therein was dipped in a phosphate buffer for 30 minutes to be sufficiently hydrated. The buffer was removed and the graft was washed three times with a fresh phosphate buffer. The hydrated graft was dipped in a cell culture broth for 30 minutes to hold a sufficient amount of the cell culture broth (a DMEM medium supplemented with 10% FBS and 1% penicillin/streptomycin), and then put into a 6-well plate for cell culture. At least 2 ml of a fresh cell culture broth was added to stabilize the graft, and fibroblasts were put on the graft at a density of $1 \times 10^5/\mu l$. The cell culture plate was safely placed for 48 hours in a cell incubator whose environment was set to grow the cells (at a constant temperature of 37° C. with supply of 5% $CO_2$). After 48 hours, the graft was carefully taken out of the plate using forceps, gently washed three times with a phosphate buffer, and then immobilized in 4% paraformaldehyde for 24 hours. The immobilized graft was soaked again in 30% sucrose for 24 hours, and an OTC block was formed. A sample block was sliced into slide fragments having a thickness of 6 µm using a microtome. The slide fragments were blocked in a phosphate buffer supplemented with 5% bovine serum albumin (BSA) and then treated with a primary antibody recognizing the fibronectin at a low temperature for 12 hours. The slide fragments were washed three times with a phosphate buffer and treated with a rhodamine B-labeled secondary antibody recognizing the primary antibody. The slide fragments were again washed three times with a phosphate buffer. In this case, the first washing was performed using a DAPI solution so as to remove the remaining secondary antibody and stain DNA with DAPI as well. One drop of a mounting solution was added to the washed slide and covered with a cover slide. Then, a rim of the cover slide was fixed using a nail polishing agent. The completed slide was observed under a fluorescent microscope.

Figure 18:
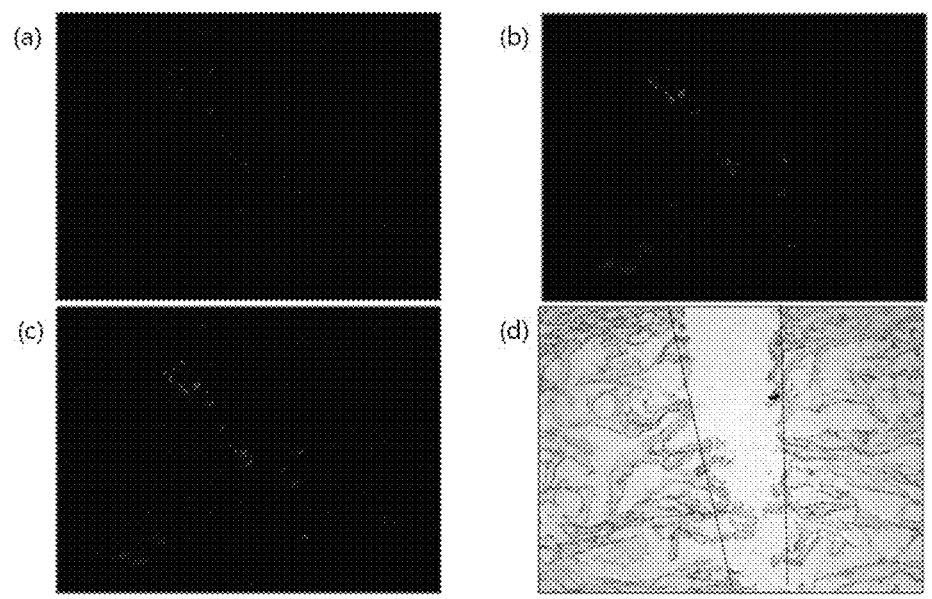
FIG. 18 is an image of the acellular dermal graft prepared in Example 2 in which effective migration of cells (fibroblasts) and activation of fibroblasts (cell proliferation, and collagen synthesis) are confirmed through double staining with 4',6-diamidino-2-phenylindole (DAPI) and fibronectin [(a) DAPI (cell DNA), (b) fibronectin, (c) DAPI fibronectin, (d) DAPI fibronectin bright field)].

As a result, it was confirmed that the cells (fibroblasts) effectively migrated, and the fibroblasts were activated (cell proliferation, and collagen synthesis) through double staining with DAPI and fibronectine (FIG. 18).

Experimental Example 6

Figure 19:
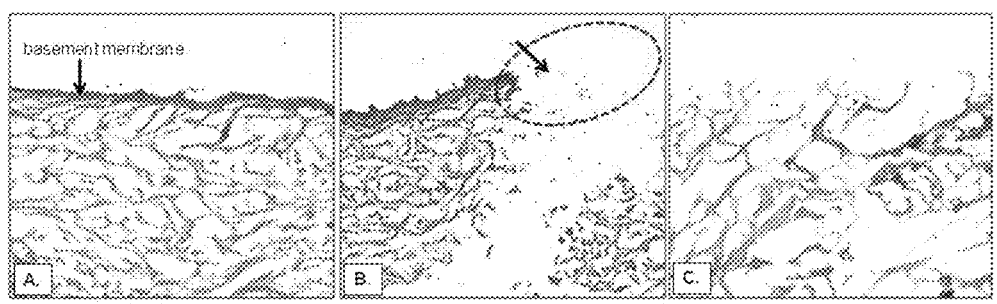
FIG. 19 shows a H&E tissue staining image of the acellular dermal graft according to the removal of the basement membrane layer (×40 magnification) [(A) a dermal graft in which the basement membrane layer is left intact, (B) an acellular dermal graft from which the basement membrane layer is partially removed, and (C) an acellular dermal graft from which the basement membrane layer is completely removed].

Comparison of Tissue Images in Terms of Presence or Absence of Basement Membrane Layer In general, the basement membrane layer is arranged in a thin and dense membrane type under an epithelial layer that is the uppermost layer of the skin, and differentiates from a dermal layer that is a layer arranged below the basement membrane layer. Also, the basement membrane layer functions as a structural cast to hold a loose dermal structure tightly and a primary barrier to infiltration of external cells differentiating from the epithelial layer. Since a basement membrane has a hard structure, it is possible to maintain a skin-grafted tissue by fixation upon tissue transplantation, but the intake of cells by the basement membrane layer may be interrupted to delay a grafting process. In this process, the hard structure of the basement membrane may cause a foreign body sensation, and tendency for inflammation and infection. On the other hand, when there is no basement membrane layer, a skin-grafted tissue may be decomposed rapidly after transplantation since the skin-grafted tissue is not stabilized structurally. When the basement membrane layer is partially removed to solve these problems, the skin-grafted tissue may be structurally stable due to the remaining basement membrane layer after transplantation, and rapid penetration of fibroblasts and formation of new blood vessels may be achieved due to the removed basement membrane layer (FIG. 19).

50 µl of fibroblasts were applied at a concentration of $5.0 \times 10^6$ cells/ml to a typical acellular dermal graft ($1 \times 1$ cm$^2$) and the acellular dermal graft of Example 6 from which the basement membrane layer was partially removed, and cultured for 24 hours to determine the state of the cells.

Figure 20:
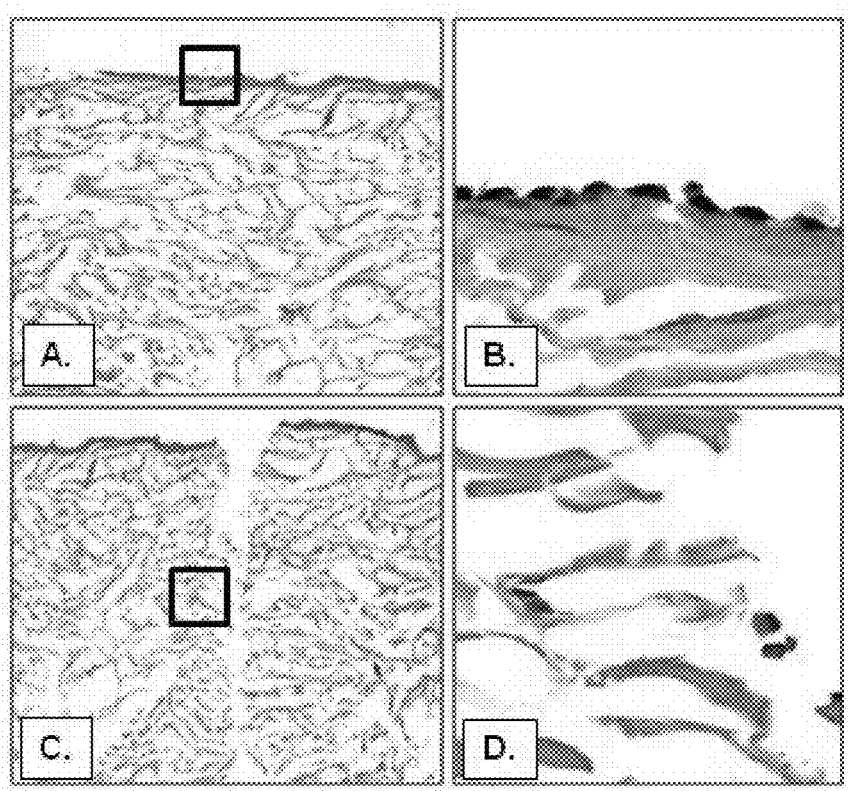
FIG. 20 shows a H&E tissue staining image (A and C: ×40 magnification, and B and D: ×400 magnification) after the cell culture of acellular dermal graft according to the removal of the basement membrane layer [(A) an acellular dermal graft in which the basement membrane layer is left intact, (B) an enlarged photo of the box shown in FIG. 20A, (C) an acellular dermal graft from which the basement membrane layer is partially removed, and (D) an enlarged photo of the box shown in FIG. 20C].

As shown in FIG. 20, it was revealed that the fibroblasts failed to penetrate upward the basement membrane layer in the case of the acellular dermal graft in which the basement membrane layer was left intact (FIG. 20B), but the fibroblasts infiltrated while maintaining the structure of the dermal tissue in the case of the acellular dermal graft from which the basement membrane layer was partially removed (FIG. 20D).

Experimental Example 7

Comparison of Electron Microscopic Images of Acellular Dermal Grafts Having a Multi-Penetration Structure Generally, the acellular dermal graft is a polymeric scaffold-type structure having a collagen fiber structure. Since some blood vessel channel remained through an acellularization process, grafting proceeded as the fibroblasts infiltrated and blood vessels were formed after transplantation. In the case of the acellular dermal graft having a multi-penetration structure, more spaces similar to the vascular channels were formed than those of the typical acellular dermal graft, indicating that the infiltration of the fibroblasts and the neovascularization resulted in more easy and rapid grafting.

Figure 21:
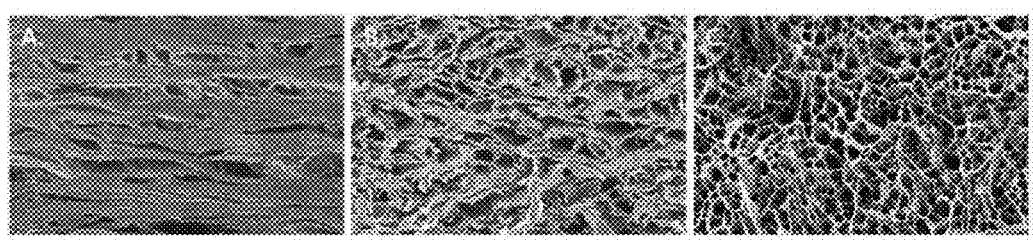
FIG. 21 shows an electron microscopic image of the acellular dermal graft (an image observed from the side; ×70 magnification) [(A) a typical acellular dermal graft, (B) an acellular dermal graft having a multi-penetration structure prepared in Example 4, and (C) an acellular dermal graft having a multi-penetration structure prepared in Example 5].

As shown in FIG. 21C, it was revealed that the infiltration of the fibroblasts and the neovascularization through a sagittal and a coronal penetrations after the transplantation were readily achieved, as observed from a side of the acellular dermal graft having a multi directional multi-penetration structure under an electron microscope.

Experimental Example 8

Confirmation of Cell Infiltration

A typical acellular dermal graft having a size of $1 \times 1$ cm$^2$, the multi-slit acellular dermal graft having the same size as typical acellular dermal graft (Example 2), and the acellular dermal graft having a porous, multi-directional multi-penetration structure (Example 5) were hydrated in sterile distilled water for transplantations. Regions of a 6-week-old Sprague-Dawley (SD) rats (male) to be transplanted were depilated using a depilator, and washed with an alcohol swab. The rats were peritoneally anesthetized with a Zoletil/Rompun mixture, and put on an operating table. Regions of the rats to be engrafted with the graft were incised to a depth of hypodermis using a surgical blade. In this case, the incision depth of the engrafted site was approximately 1.5 cm. The hydrated graft was transplanted into the engrafted site using sterile forceps, and carefully sutured using a sterile stitching fiber. The engrafted region was sterilized with an alcohol swab or an iodine solution to prevent a secondary infection of the incised region after the suturing. After 4 weeks of the transplantation, the transplanted acellular dermal tissue was sampled from the rat, a paraffin block was prepared, and tissue fragments having a thickness of 5 µm were prepared, and stained with an H&E stain. Based on the H&E staining results, the number of fibroblasts infiltrating into the acellular dermal tissue were counted.

Figure 22:
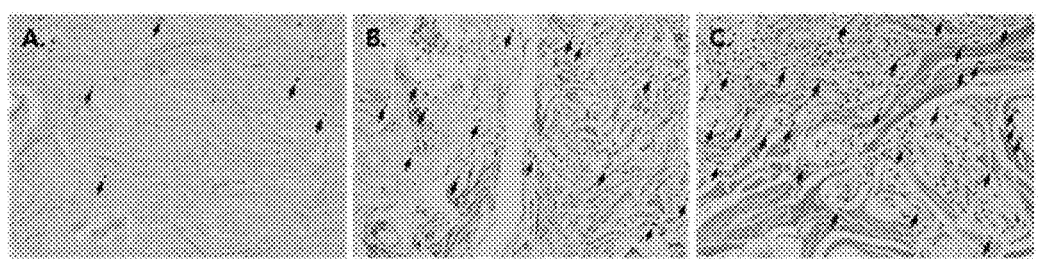
FIG. 22 shows a H&E tissue staining image of the acellular dermal graft after 4-week transplantation (arrows: infiltrated fibroblasts; ×100 magnification) [(A) a typical acellular dermal graft, (B) a multi-slit acellular dermal graft prepared in Example 2, and (C) an acellular dermal graft having a multi-penetration structure prepared in Example 5].
Figure 23:
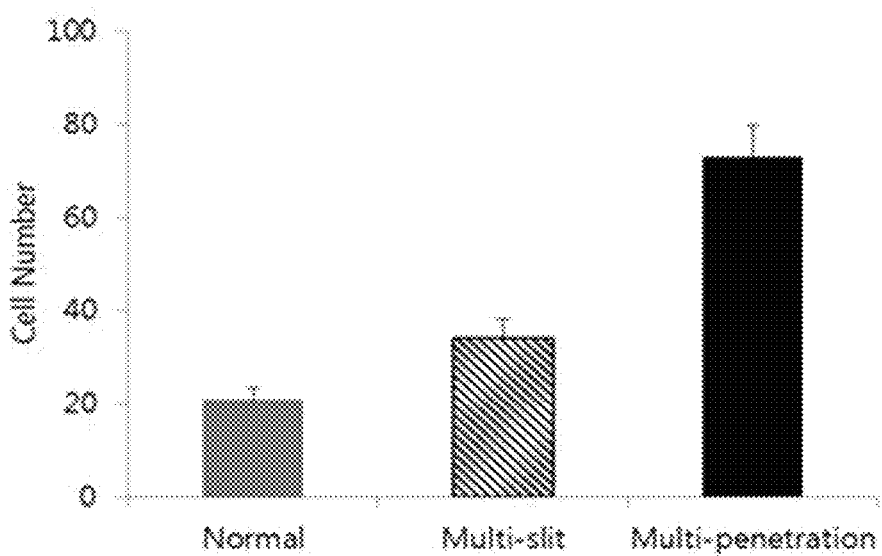
FIG. 23 shows the results obtained by measuring the cell number of fibroblasts infiltrated into the acellular dermal graft after 4-week transplantation [Normal: a typical acellular dermal graft, Multi-slit: a multi-slit acellular dermal graft prepared in Example 2, and Multi-penetration: an acellular dermal graft having a multi-penetration structure prepared in Example 5].

As a result, as shown in FIGS. 22 and 23, it was revealed that the cell penetration in the case of acelluar dermal graft of Example 5 (Multi-penetration) occurred better than that of the acellular dermal graft of Example 2 (Multi-slit), indicating that rapid infiltration of the fibroblasts was more advantageous to regeneration into autologous tissues.

Experimental Example 9

Confirmation of Neovascularization

The newly formed blood vessels in each of the transplanted acellular dermal tissues were counted, based on the H&E staining results as described in Example 8.

Figure 24:
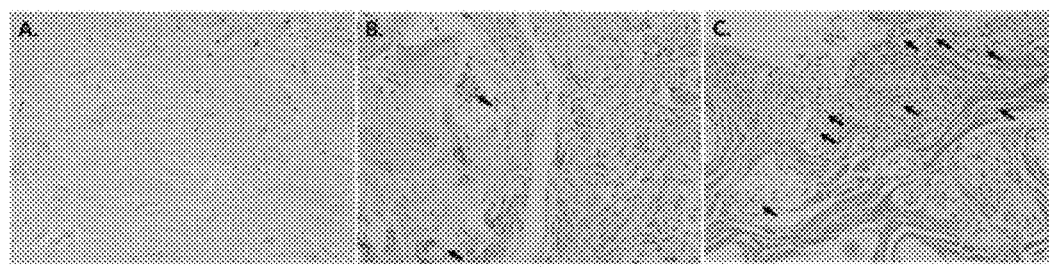
FIG. 24 shows a H&E tissue staining image of the acellular dermal graft after 4-week transplantation (arrows: neovascularizations; ×100 magnification), showing that new blood vessels are formed after transplantation of acellular dermal tissues (indicated by arrows): (A) a typical acellular dermal graft, (B) a multi-slit acellular dermal graft prepared in Example 2, and (C) an acellular dermal graft having a multi-penetration structure prepared in Example 5.
Figure 25:
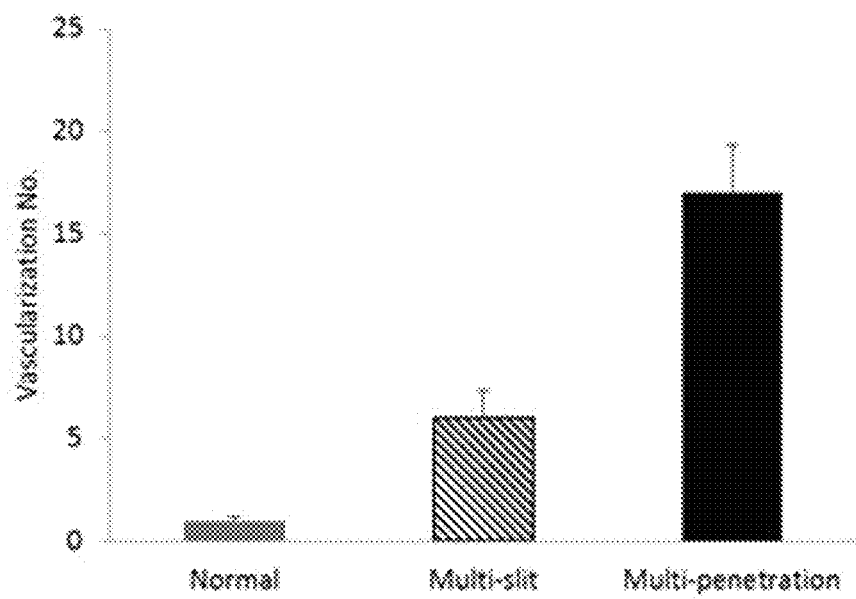
FIG. 25 shows the results obtained by measuring the vascularization number of the acellular dermal graft after 4-week transplantation [Normal: a typical acellular dermal graft, Multi-slit: a multi-slit acellular dermal graft prepared in Example 2, and Multi-penetration: an acellular dermal graft having a multi-penetration structure prepared in Example 5].

As a result, as shown in FIGS. 24 and 25, it was revealed that the neovascularization in the case of the acellular dermal graft of Example 5 (Multi-penetration) occurred better than that of the acellular dermal graft of Example 2 (Multi-slit), indicating that the rapid neovascularization was more advantageous to regeneration into autologous tissues.

The acellular dermal graft according to the present invention can have conditions very suitable for transplantation in a human body, that is, swift formation and sufficient proliferation of new blood vessels, an increase in proliferation and uptake of fibroblasts, inhibition of dead space formation, prevention of bodily fluid retention, stable immobilization of a graft in a host tissue, an increase in a graft area due to increased flexibility of the graft, a decrease in pain after surgery, and prevention of skin necrosis, an inflammatory response and infections caused by decreased blood flow to the skin and a subcutaneous tissue of a site coming in contact with the graft.

In particular, when surgery is performed by inserting a graft under a subcutaneous tissue, the convenience of surgery can be improved, and a smooth external appearance can also be maintained as the skin lined on the graft does not protrude after the transplantation. Also, it is possible to discriminate between the front and rear surfaces of the graft.

While the invention has been shown and described with reference to certain exemplary embodiments thereof, it will be understood by those skilled in the related art that various changes in form and details may be made therein without departing from the scope of the invention as defined by the appended claims.

What is claimed is:

1. An acellular dermal graft having multi directional multi-penetrations formed therein,
   wherein the multi directional multi-penetrations have a multi-penetration structure along a vertical axis, and a horizontal-axis multi-penetration structure in which layers are alternately stacked so that transversally aligned penetrations are formed in one layer and longitudinally aligned penetrations are formed in another layer.

2. The acellular dermal graft of claim 1, wherein a basement membrane layer is totally or partially removed.

3. The acellular dermal graft of claim 1, wherein corner portions are subjected to slope cutting.

4. The acellular dermal graft of claim 1, wherein the acellular dermal graft is skin, ligament, or cartilage.

5. A method of preparing an acellular dermal graft, comprising: forming multi directional multi-penetrations, wherein the multi directional multi-penetrations have a multi-penetration structure along a vertical axis, and a horizontal-axis multi-penetration structure in which layers are alternately stacked so that transversally aligned penetrations are formed in one layer and longitudinally aligned penetrations are formed in another layer.

6. The method of claim 5, comprising:
removing an epidermis;
removing dermal cells;
forming multi directional multi-penetrations; and
performing cryopreservation.

7. The method of claim 6, further comprising:
removing the basement membrane layer totally or partially after removing the dermal cells.

8. The method of claim 6, further comprising:
slope-cutting corner portions after performing cryopreservation.

9. An acellular dermal graft prepared using the method of claim 5.

10. A therapeutic agent for treating skin injuries, comprising the acellular dermal graft of claims 1.

* * * * *